(12) United States Patent
Zheng

(10) Patent No.: US 9,096,688 B2
(45) Date of Patent: Aug. 4, 2015

(54) METHOD FOR PRODUCING A COLLAGEN MEMBRANE AND USES THEREOF

(71) Applicant: University of Western Australia, Nedlands (AU)

(72) Inventor: Ming Hao Zheng, City Beach (AU)

(73) Assignee: Orthocell Pty Ltd. (AU)

( * ) Notice: Subject to any disclaimer, the term of this patent is extended or adjusted under 35 U.S.C. 154(b) by 0 days.

(21) Appl. No.: 14/219,555

(22) Filed: Mar. 19, 2014

(65) Prior Publication Data

US 2014/0288271 A1 Sep. 25, 2014

Related U.S. Application Data

(63) Continuation of application No. PCT/AU2013/000621, filed on Jun. 12, 2013.

(30) Foreign Application Priority Data

Jun. 12, 2012 (AU) ................ 2012902458

(51) Int. Cl.
| | | |
|---|---|---|
| C07K 1/113 | (2006.01) |
| C07K 14/78 | (2006.01) |
| A61K 38/39 | (2006.01) |
| A61L 27/36 | (2006.01) |
| A61K 38/00 | (2006.01) |
| A61F 2/18 | (2006.01) |

(52) U.S. Cl.
CPC ............. *C07K 14/78* (2013.01); *A61L 27/3604* (2013.01); *A61L 27/3683* (2013.01); *C07K 1/1136* (2013.01); *A61F 2002/183* (2013.01); *A61L 2430/14* (2013.01)

(58) Field of Classification Search
CPC .................................................. C07K 1/1136
See application file for complete search history.

(56) References Cited

U.S. PATENT DOCUMENTS

| | | | | |
|---|---|---|---|---|
| 6,565,960 B2 * | 5/2003 | Koob et al. | ........... | 428/304.4 |
| 2008/0161917 A1 * | 7/2008 | Koob et al. | ........... | 623/13.11 |
| 2012/0093877 A1 * | 4/2012 | Zheng | ........... | 424/400 |

FOREIGN PATENT DOCUMENTS

| | | |
|---|---|---|
| WO | WO 2007/060459 A2 | 5/2007 |
| WO | WO 2010009511 A1 * | 1/2010 |
| WO | WO 2011/007152 A1 | 1/2011 |

OTHER PUBLICATIONS

Yang, L. (2008) "Mechanical properties of collagen fibrils and elastic fibers explored by AFM", (1979) Dissertation of University of Twente, pp. 1-512.*
Kronick et al. (1998) Destabilization of collagen in hide and leather by anionic surfactants. II. Calorimetry of the reaction of collagen with sulfates, J. Polym. Sci. B: Polym. Phys., vol. 36, pp. 805-813.*
Usha et al. (2008) Stability of collagen with polyols against guanidine denaturation, Colloids Surf. B Biointerfaces, vol. 61, No. 1, pp. 39-42.*
Crapo et al. "An overview of tissue and whole organ decellularization processes", Biomaterials, Apr. 2011, 32(12), 3233-3243.

* cited by examiner

*Primary Examiner* — Manjunath Rao
*Assistant Examiner* — Samuel Liu
(74) *Attorney, Agent, or Firm* — Baker & Hostetler LLP

(57) ABSTRACT

The present invention relates to a method of producing a collagen membrane that has particular mechanical properties. In particular, the present invention relates to a method A of producing a collagen membrane comprising the steps of (i) isolating a collagen-containing tissue and incubating same in an ethanol solution; (ii) incubating the collagen-containing tissue from step (i) in a first solution comprising an inorganic salt and an anionic surfactant in order to denature non-collagenous proteins contained therein; (iii) incubating the collagen-containing tissue produced in step (ii) in a second solution comprising an inorganic acid until the collagen in said material is denatured; and (iv) incubating the collagen-containing tissue produced in step (iii) in a third solution comprising an inorganic acid with simultaneous mechanical stimulation for sufficient time to enable the collagen bundles in said collagen-containing tissue to align; wherein the mechanical stimulation comprises applying tension cyclically to the collagen-containing tissue.

23 Claims, 11 Drawing Sheets

K.

L.

| Group | 3 days (n=5) | 5 days (n=5) | 7 days (n=5) | 9 days (n=5) | 14 days (n=5) | 28 days (n=5) |
|---|---|---|---|---|---|---|
| ACS | 0/5 (0.0%) | 0/5 (0.0%) | 3/5 (60.0%)* | 5/5 (100%)* | 5/5 (100%) | 5/5 (100%) |
| Paper patch | 0/5 (0.0%) | 0/5 (0.0%) | 2/5 (40.0%) | 5/5 (100%)* | 5/5 (100%) | 5/5 (100%) |
| Gelfoam | 0/5 (0.0%) | 0/5 (0.0%) | 0/5 (0.0%) | 3/5 (60.0%) | 5/5 (100%) | 5/5 (100%) |
| Control | 0/5 (0.0%) | 0/5 (0.0%) | 0/5 (0.0%) | 2/5 (40.0%) | 4/5 (80.0%) | 5/5 (100%) |

*$p<0.05$, statistically significant difference between control (spontaneous healing) and the other scaffold.

Figure 10

METHOD FOR PRODUCING A COLLAGEN MEMBRANE AND USES THEREOF

CROSS-REFERENCE TO RELATED APPLICATIONS

This application is a continuation application of PCT/AU2013/000621, filed Jun. 12, 2013, which claims benefit of Australian patent application 2012902458, filed Jun. 12, 2012, the entire contents of which are incorporated herein by reference.

FIELD

The present invention relates to a method of producing a collagen membrane that has particular mechanical properties. In particular, the present invention relates to a method of producing a collagen membrane which comprises treating a collagen-containing tissue with inorganic salts and anionic surfactants sufficient to produce specific mechanical properties.

BACKGROUND

Collagen and its derived products are used extensively in the production of collagen-containing implantable scaffolds. Collagen is well recognized as a material that has low antigenicity, is biodegradable and has good mechanical, haemostatic and cell-binding properties (Sheu et al., (2001), *Biomaterials*, 22(13):1713-9; Pieper et al., (2002), *Biomaterials*, 23(15):3183-92; Chvapil et al., (1973), *Int Rev Connect Tissue Res.*, 6:1-61; Pachence (1996), *J. Biomed. Mater. Res.*; 33(1):35-40; and Lee et al., (2001), *Int J Pharm.*; 221(1-2): 1-22), which enables it to be used to replace or repair tissue temporarily or permanently. Collagen scaffolds are routinely used a substrate upon which cells are able to proliferate and differentiate and being eventually replaced by normal tissue.

However, it is also well known that collagen-containing scaffolds can provoke inflammation and/or fibrosis when implanted. See, for example, Wisniewski et al., (2000), *J. Anal Chem.*; 366 (6-7) (p. 611-621). As a consequence, collagen-containing scaffolds are typically chemically or physically treated (cross linked) to confer mechanical strength and resistance to enzymatic (collagenase) degradation. There are several cross-linking strategies that have been used on collagen-containing materials. Glutaraldehyde is the most widely used cross-linking agent (Sheu et al., (2001) supra; Barbani et al., (1995), *J Biomater. Sci. Polym. Ed.*; 7(6):461-9). However, glutaraldehyde and its reaction products are associated with cytotoxicity in vivo, due to the presence of cross-linking by-products and the release of glutaraldehyde-linked collagen peptides during enzymatic degradation (Huang-Lee et al., (1990), *J Biomed Mater Res.*, 24(9):1185-201; van Luyn et al., (1992), *Biomaterials*, 13(14):1017-24.

In order to avoid in vivo cytotoxicity of glutaraldehyde cross-linked collagen, several alternative compounds have been examined as potential collagen cross-linking agents (Khor (1997), *Biomaterials*, 18(2): 95-105; Sung et al. (1996), *Biomaterials*; 17(14): 1405-10) such as polyepoxy, hexamethylene diisocyanate (HMDI), 1-ethyl-3-(3-dimethylamino-propyl)carbodiimide (EDC), and ultra-violet (UV) or gamma-ray irradiation. Koob et al., (2001), *J Biomed Mater Res.*, 56(1):31-48 showed that nordihydroguaiaretic acid (NDGA) significantly improved the mechanical properties of synthetic collagen fibres. In addition, they showed that NDGA cross-linked collagen fibres did not elicit a foreign body response nor did they stimulate an immune reaction during six weeks in vivo.

However, despite all of these advancements there remain issues with using cross-linked collagen as well as native collagen. Thus, there is still a need for a collagen-containing scaffold that has the following properties:
a) pores that interconnect in such a way as to favour tissue integration and vascularisation;
b) biodegradability and/or bioresorbability so that normal tissue ultimately replaces the scaffold;
c) surface chemistry that promotes cell attachment, proliferation and differentiation;
d) strength and flexibility; and
e) low antigenicity.

One area that has a particular need for a replacement collagen-containing tissue is the repair of tympanic membrane (TM) perforations. If left untreated, TM perforations can result in hearing loss, recurrent otorrhea, possible middle ear infection and acquired cholesteatoma (Parekh et al., (2009), *The Laryngoscope*; 119:1206-1213). Although most acute TM perforations heal spontaneously, large or chronic TM perforations, especially from chronic suppurative otitis media, often fail to heal and may require grafting (Lindeman et al., (1987), *Archives of Otolaryngology—Head and Neck Surgery*; 113:1285).

Currently, surgical methods such as myringoplasty are regarded as the most effective and reliable treatment for TM perforations (Sheehy et al., (1980), *The Annals of otology, rhinology, and laryngology*; 89:331; Karela et al., (2008), *European Archives of Oto-Rhino-Laryngology*; 265: 1039-1042). Various autologous grafts and allografts such as muscle fascia, cartilage, perichondrium and AlloDerm have been used, however, all have their own limitations (Levin et al., (2009), *Expert review of medical devices*; 6:653-664). For instance, temporalis fascia, which is regarded as the "gold standard", is associated with donor site morbidity, additional incisions, long operation time and a shortage of material in revision cases (Levin et al., (2009), supra). To date, a range of xenografts and synthetic materials, including GELFOAM® membrane (Abbenhaus, (1978), *Otolaryngology*; 86:ORL485), paper patch (Golz et al., (2003), *Otolaryngology—Head and Neck Surgery*; 128: 565) and hyaluronic acid derivatives (Teh et al., (2011), *Expert Opinion on Biological Therapy*; 1-14) have been investigated as suitable scaffolds to support the regeneration of TM. However, there is little evidence to support any of these as optimal materials for various types of perforations.

Moreover, several commercially available xenografts such as porcine small intestinal submucosa, contain xeno DNA materials and evoke an inflammatory response due to the remnant xenocellular components including serotonin. In addition, synthetic materials are non-biodegradable, and their biomechanical and material properties are different compared to the normal TM, which may affect the long-term hearing function (Levin et al., (2009), supra). Hence, there is a constant search for better materials to achieve improved healing and hearing.

SUMMARY

The present invention provides a method of producing a collagen-containing tissue which has reduced inflammation and/or fibrosis when implanted compared to other collagen-containing tissue. In some embodiments, the collagen-containing tissue not cross-linked.

Thus, in a first aspect the present invention provides a method of producing a collagen membrane comprising the steps of:
(i) isolating a collagen-containing tissue and incubating same in an ethanol solution;
(ii) incubating the collagen-containing tissue from step (i) in a first solution comprising an inorganic salt and an anionic surfactant in order to denature non-collagenous proteins contained therein;
(iii) incubating the collagen-containing tissue produced in step (ii) in a second solution comprising an inorganic acid until the collagen in said material is denatured; and
(iv) incubating the collagen-containing tissue produced in step (iii) in a third solution comprising an inorganic acid with simultaneous mechanical stimulation for sufficient time to enable the collagen bundles in said collagen-containing tissue to align;
wherein the mechanical stimulation comprises applying tension cyclically to the collagen-containing tissue.

It will be appreciated that any inorganic salt may be used in the first solution as long as it is capable of forming a complex with Lewis acids. In some embodiments, the inorganic salt is selected from the group consisting of trimethylammonium chloride, tetramethylammonium chloride, sodium chloride, lithium chloride, perchlorate and trifluoromethanesulfonate. In other embodiments, the inorganic salt is lithium chloride (LiCl).

While any number of anionic surfactants may be used in the first solution, in some embodiments, the anionic surfactant is selected from the group consisting of alkyl sulfates, alkyl ether sulfates, alkyl sulfonates, and alkyl aryl sulfonates. Particularly useful anionic surfactants include alkyl sulphates such as sodium dodecyl sulphate (SDS).

In some embodiments, the first solution comprises about 1% (v/v) SDS and about 0.2% (v/v) LiCl.

In some embodiments, the inorganic acid in the second solution comprises about 0.5% (v/v) HCl, while the inorganic acid in the third solution comprises about 1% (v/v) HCl.

It will be appreciated by those skilled in the art that the incubation periods in each of the three steps will vary depending upon: (i) the type of collagen-containing tissue; (ii) the type of inorganic salt/acid and/or anionic surfactant; (iii) the strength (concentration) of each inorganic salt/acid and/or anionic surfactant used and (iv) the temperature of incubation. In some embodiments, the incubation period in step (i) is at least 8 hours. In other embodiments, the incubation period in step (ii) is less than 60 minutes, while in other embodiments the incubation period in step (iii) is at least 20 hours.

In some embodiments, the incubation in step (ii) is at about 4° C. In other embodiments, the incubation in step (ii) is undertaken for at least 12 hours.

In some embodiments, the second solution comprises about 0.5% (v/v) HCl.

In some embodiments, the incubation in step (iii) is undertaken for about 30 minutes. In other embodiments, the incubation in step (iii) is undertaken with shaking.

In some embodiments, the third solution comprises about 1% (v/v) HCl solution.

In some embodiments, the incubation in step (iv) is undertaken for about 12 to 36 hours, preferably for about 24 hours. In other embodiments, the incubation in step (iv) is undertaken with shaking.

In some embodiments, the methods of the invention further comprises a neutralization step between step (iii) and step (iv) which comprises incubation of said collagen-containing tissue with about 0.5% (v/v) NaOH.

In some embodiments, the methods of the invention further comprises step (v) which comprises incubating the collagen-containing tissue from step (iv) with acetone and then drying the collagen-containing tissue.

In some embodiments, the methods of the invention further comprises between steps (ii) and (iii) and/or between steps (iii) and (iv) a step of contacting the collagen-containing tissue with glycerol in order to visualise and facilitate the removal of fat and/or blood vessels.

The glycerol may be contacted with the collagen-containing tissue for any amount of time that will facilitate the removal of fat and/or blood vessels. In some embodiments, the contact time is at least 10 minutes.

In some embodiments, the methods of the invention further comprises between steps (ii) and (iii) and/or between steps (iii) and (iv) a wash step for the collagen-containing tissue. The purpose of the wash step used between steps (ii) and (iii) is to remove denatured proteins. Thus, any wash solution capable of removing denatured proteins can be used. In some embodiments the wash solution used between steps (ii) and (iii) is acetone.

Following the washing with acetone, the collagen-containing tissue is further washed with sterile water.

In some embodiments, the collagen-containing tissue is further washed in a NaOH:NaCl solution. If the collagen-containing tissue is washed with NaOH:NaCl it is then preferably washed with sterile water.

In some embodiments, after step (iv) the collagen-containing tissue is further washed with the first solution.

It will be appreciated by those skilled in the art that the collagen-containing tissue can be any tissue isolated from a mammalian animal. However, it will also be appreciated that the collagen-containing tissue will comprise dense connective tissue. In some embodiments, the collagen-containing tissue is isolated from a sheep, a cow, a pig or a human. Preferably, the collagen-containing tissue is isolated from a human.

In some embodiments, the collagen-containing tissue is autologous.

In a second aspect, the present invention provides a collagen membrane produced by a method to the first aspect, wherein said membrane produced by the method comprises greater than 80% (w/w) type I collagen fibres or bundles having a knitted structure and a modulus of greater than 300 MPa.

In some embodiments, the collagen membrane will have a modulus of greater than 400 MPa and preferably greater than 500 MPa.

The collagen membrane will also have an extension at maximum load of less than 85%, preferably less than 80%.

In a third aspect, the present invention provides a method for preparing a device for implantation into the body or tissue of a person or animal, said method comprising placing a collagen membrane on said device, wherein said collagen membrane is produced by a method comprising:
(i) isolating a collagen-containing tissue and incubating same in an ethanol solution;
(ii) incubating the collagen-containing tissue from step (i) in a first solution comprising an inorganic salt and an anionic surfactant in order to denature non-collagenous proteins contained therein;
(iii) incubating the collagen-containing tissue produced in step (ii) in a second solution comprising an inorganic acid until the collagen in said material is denatured; and
(iv) incubating the collagen-containing tissue produced in step (iii) in a third solution comprising an inorganic acid with simultaneous mechanical stimulation for sufficient time to enable the collagen bundles in said collagen-containing tissue to align;

wherein the mechanical stimulation comprises applying tension cyclically to the collagen-containing tissue.

In a fourth aspect the present invention provides a device having enhanced biocompatibility for implantation into the body or tissue of a person or animal, wherein said device comprises a collagen membrane is produced by a method comprising:
(i) isolating a collagen-containing tissue and incubating same in an ethanol solution;
(ii) incubating the collagen-containing tissue from step (i) in a first solution comprising an inorganic salt and an anionic surfactant in order to denature non-collagenous proteins contained therein;
(iii) incubating the collagen-containing tissue produced in step (ii) in a second solution comprising an inorganic acid until the collagen in said material is denatured; and
(iv) incubating the collagen-containing tissue produced in step (iii) in a third solution comprising an inorganic acid with simultaneous mechanical stimulation for sufficient time to enable the collagen bundles in said collagen-containing tissue to align;

wherein the mechanical stimulation comprises applying tension cyclically to the collagen-containing tissue.

Once produced, the collagen membrane produced by the methods of the present invention can be used to repair various tissue defects.

Accordingly, in a fifth aspect the present invention provides use of a collagen membrane according to the first or second aspect or a device according to the fourth aspect for the repair of a tissue defect in a mammalian animal.

In a sixth aspect, the present invention provides a method of treating a tissue defect in a mammalian animal subject comprising the step of inserting a collagen membrane according to the first or second aspect or a device according to the fourth aspect into said tissue defect.

The methods of the present invention can be used to produce collagen membranes of various thicknesses depending upon their end use. For example, membranes for use in the repair of tympanic membranes in non-human animals might be 50 µm thick, while repair of tympanic membranes in humans might be 100 µm thick. Thus, various membrane thicknesses are envisaged.

In a seventh aspect, the present invention provides a collagen membrane produced by the method of the first aspect that is at least 10 µm. Preferably, the membrane is between about 10 µm and 400 µm thick. More preferably, between 50 µm and 200 µm thick. In some embodiments, the collagen membrane of the present invention is about 100 µm thick.

In an eighth aspect the present invention provides a method of repairing a tympanic membrane perforation comprising the step of inserting a collagen membrane according to the first or second aspect or a device according to the fourth aspect into or adjacent to said tympanic membrane perforation.

In some embodiments, the method of the first or second aspects has the proviso that no cross-linking of the collagen-containing tissue takes place. In some embodiments, the method of the first or second aspects has the proviso that no glutaraldehyde is used in the methods of the present invention.

BRIEF DESCRIPTION OF THE FIGURES

FIG. 10 shows healing of tympanic membrane perforation at different time points following grafting.

Figure 1:
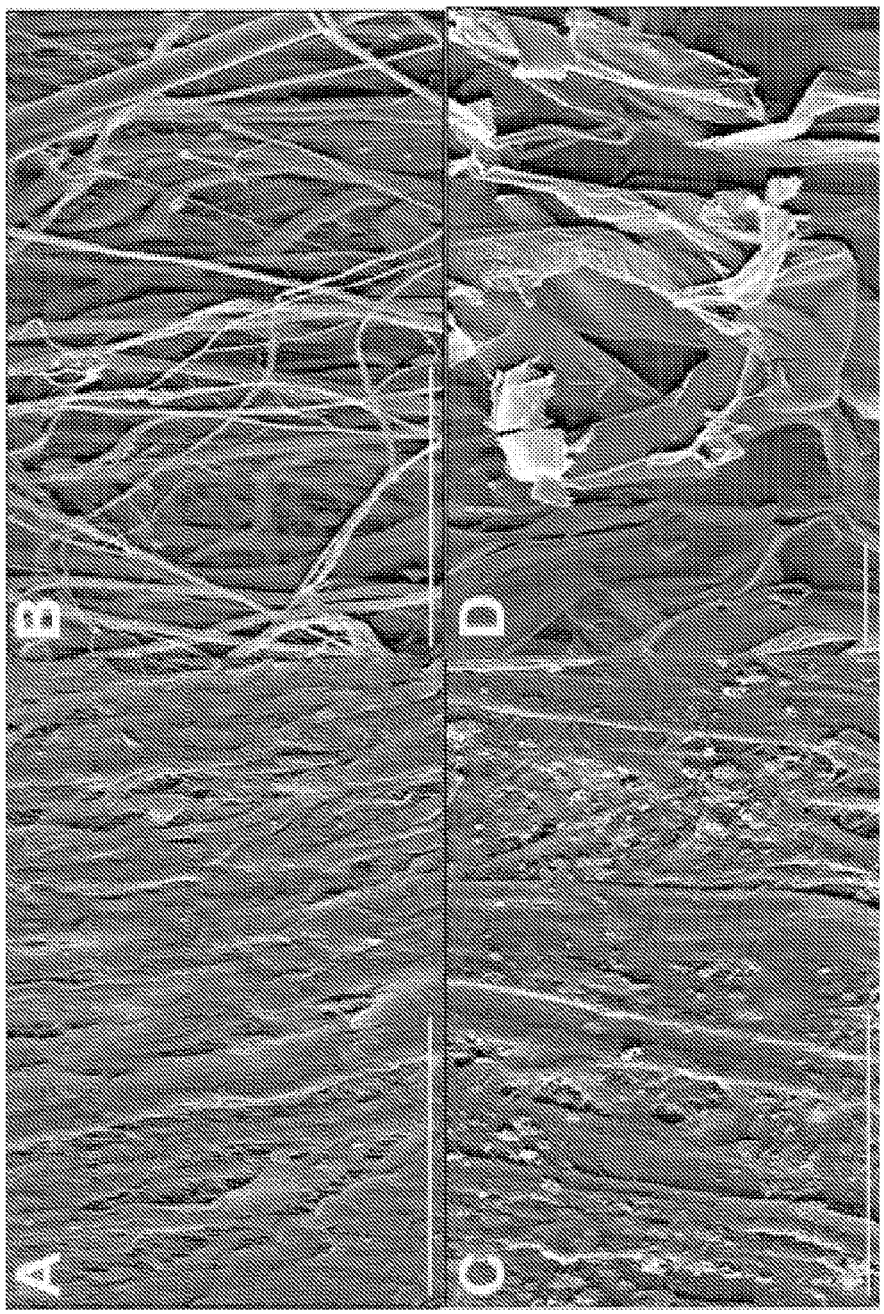
FIG. 1 shows the surface morphology of the collagen membrane produced by the methods of the present invention (TYMPACOL™ membrane referred to as ACS herein) compared to other membranes. Scanning electron microscopy shows the surface morphology of three membranes (Panel A-C; ×500, D; ×200). TYMPACOL™ membrane (referred to as ACS in FIG. 1) possesses two distinct surfaces, a smooth surface featuring compact collagen bundles (Panel A), and a rough, porous surface of loose collagen fibres (Panel B). Paper patch (membrane) surface is uneven with few small pores (Panel C). GELFOAM® membrane shows substantial pores of varying sizes (Panel D). Scale bar: 500 µm.

Further features, advantages and details of the present invention will be appreciated by those of ordinary skill in the art from a reading of the figures and the detailed description of the embodiments that follow, such description being merely illustrative of the present invention.

DETAILED DESCRIPTION OF THE PREFERRED EMBODIMENTS OF THE INVENTION

Generally stated, embodiments of the subject invention are directed to collagen membrane, coverings, coatings and/or scaffolds which are particularly suitable for implantable medical devices, and methods of making and using the same in animal or human patients. The patient can be a human or other animal, such as a primate, equine, bovine, ovine, canine, or feline animal. The collagen membrane, coatings, coverings and/or scaffolds can be provided as a tissue-contacting surface which may encapsulate all or a portion of the implantable devices to thereby provide a reduced immunogenic response and/or long-lived in vivo functionality of the implanted device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y". As used herein, phrases such as "from about X to Y" mean "from about X to about Y".

The term "about" as used herein refers to a deviation in the value following the term by 10% above or below. For example, reference to about 70% ethanol includes ranges between 63% and 77% i.e. 10% below or above the 70% value. This includes 64%, 65%, 66%, 67%, 68%, 69%, 70%, 71%, 72%, 73%, 74%, 75%, 76% and 77% ethanol.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "implantable" means the "collagen-containing tissue", "collagen membrane", "device" or "scaffold" can be inserted, embedded, grafted or otherwise acutely or chronically attached or placed on or in a patient. The term "collagen-containing tissue" means skin, muscle and the like which can be isolated from a mammalian body that contains collagen. The term "collagen-containing tissue" also encompasses "synthetically" produced tissue in which collagen or collagen containing material has been assembled or manufactured outside a body.

The term "collagen membrane" is intended in this connection to be understood to mean a membrane chiefly based on collagen. A "membrane" typically comprises the components as described herein.

The term "chronically" means that the "collagen-containing tissue", "collagen membrane", "device" or "scaffold" is configured to remain implanted for at least 2 months, typically at least 6 months, and in some embodiments, one or more years while remaining operational for its intended function. The terms "coating" or "covering" refer to a material on a target surface of the membrane, device or scaffold. The coating can be a porous coating that can inhibit cell and tissue fouling of the underlying membrane, device or scaffold. The coating may not promote tissue growth. The coating can be a thin or thick film, foam or other barrier to tissue fouling and biodegradation. The term "scaffold" refers to a porous material and/or structure into which cells, tissue, vessels, etc, can grow into, colonize and populate.

Collagen bundles are composed of collagen fibres. Collagen fibres are composed of three polypeptide chains that intertwine to form a right-handed triple helix. Each collagen polypeptide chain is designated as an $\alpha$ chain and is rich in glycine, proline and hydroxyproline. There are a number of different $\alpha$ chains and different combinations of these $\alpha$ chains correspond with different types of collagen. In some embodiments, the collagen membrane of the present invention comprises type I collagen. Type I collagen is composed of two $\alpha 1$ chains and one $\alpha 2$ chain.

In some embodiments, the collagen fibres or bundles are provided from dense connective tissue isolated from a source. The term "dense connective tissue" as used herein refers to the matrix comprised primarily of type I collagen fibres or bundles found in the tendons, ligaments and dermis of all mammals. Dense connective tissue is distinct from "loose connective tissue". Loose connective tissue is characterised by loosely arranged fibres and an abundance of cells and is present, for example, beneath the epithelia that covers body surfaces and lines internal organs.

Dense connective tissue may be regular or irregular. Dense regular connective tissue provides strong connection between different tissues and is found in tendons and ligaments. The collagen fibres in dense regular connective tissue are bundled in a parallel fashion. Dense irregular connective tissue has fibres that are not arranged in parallel bundles as in dense regular connective tissue and comprises a large portion of the dermal layer of skin. The collagen membrane of the present invention may be composed of either regular dense connective tissue or dense irregular connective tissue, or a combination of both.

Collagen "microfibrils," "fibrils," "fibres," and "natural fibres" refer to naturally-occurring structures found in a tendon. Microfibrils are about 3.5 to 50 nm in diameter. Fibrils are about 50 nm to 50 µm in diameter. Natural fibres are above 50 µm in diameter. A "synthetic fibre" refers to any fibre-like material that has been formed and/or chemically or physically created or altered from its naturally-occurring state. For example, an extruded fibre of fibrils formed from a digested tendon is a synthetic fibre but a tendon fibre newly harvested from a mammal is a natural fibre. Of course, synthetic collagen fibres can include non-collagenous components, such as hydroxyapatite or drugs that facilitate tissue growth. For example, the compositions can contain growth factors such as basic fibroblast growth factor, tumour growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. Of course, synthetic collagen fibres can include non-collagenous components, such as particulates, hydroxyapatite and other mineral phases, or drugs that facilitate tissue growth. For example, the compositions can contain carbon nano-tubes, zinc nano-wires, nano-crystalline diamond, or other nano-scale particulates; larger crystalline and non-crystalline particulates such as calcium phosphate, calcium sulfate, apatite minerals. For example, the compositions can contain therapeutic agents such as bisphosphonates, anti-inflammatory steroids, growth factors such as basic fibroblast growth factor, tumour growth factor beta, bone morphogenic proteins, platelet-derived growth factor, and insulin-like growth factors; chemotactic factors such fibronectin and hyaluronan; and extracellular matrix molecules such as aggrecan, biglycan, and decorin.

The term "source" as used herein refers to any collagen tissue containing dense connective tissue in any mammal. In some embodiments, the tissue containing dense connective tissue is a tendon. A tendon is the tissue which connects muscle to bone in a mammal.

In some embodiments, the collagen-containing tissue may be isolated from any mammalian animal including, but not limited to a sheep, a cow, a pig or a human. In other embodiments, the collagen-containing tissue is isolated from a human.

In some embodiments, the collagen-containing tissue is "autologous", i.e. isolated from the body of the subject in need of treatment.

In some embodiments, the present invention provides a collagen membrane comprising greater than 80% type I collagen. In other embodiments, the collagen membrane comprises at least 85% type I collagen. In still other embodiments the collagen membrane comprises greater than 90% type I collagen.

The collagen fibres or bundles of the collagen membrane form a knitted structure. The term "knitted structure" as used herein refers to a structure comprising first and second groups of fibres or bundles where fibres or bundles in the first group extend predominately in a first direction and fibres or bundles in the second group extend predominately in a second direction, where the first and second directions are different to each other and the fibres or bundles in the first group interleave or otherwise weave with the fibres or bundles in the second group. The difference in direction may be about 90°.

The term "maximum tensile load strength" as used herein refers to the maximum tensile load that the collagen membrane can bear. On a Load v Extension curve this is represented by the peak load on the curve.

In some embodiments, the collagen membrane has maximum tensile load strength of greater than 20 N. In some embodiments, the collagen membrane of the present invention has maximum tensile load strength greater than 25 N, 40 N, 60 N, 80 N, 100 N, 120 N or 140 N.

Further, it is believed that the knitted structure of the embodiments of the collagen membrane provides reduced extension at maximum load of the bioscaffold while providing an increase in modulus.

The term "modulus" as used herein means Young's Modulus and is determined as the ratio between stress and strain. This provides a measure of the stiffness of the collagen membrane.

In some embodiments the collagen membrane has a modulus of greater than 100 MPa. In other embodiments the collagen membrane has a modulus of greater than 200 MPa, 300 MPa, 400 MPa, or 500 MPa.

The term "extension at maximum load" as used herein means the extension of the collagen membrane at the maximum tensile load strength referenced to the original length of the collagen membrane in a non-loaded condition. This is to be contrast with maximum extension which will be greater.

In some embodiments, the collagen membrane has extension at maximum load of less than 85% of the original length.

Examples of devices that can benefit from the collagen membrane, collagen coatings and/or scaffolds contemplated by embodiments of the invention, include, but are not limited to, implantable stents, including cardiac, arterial, neuro (brain), urinary, and other stents, implantable power generators (IPGs), pacemakers, defibrillators, cardioverters, stimulators and/or lead systems for the brain, central nervous system (CNS) or peripheral nervous system, cardiac or other biological system, cardiac replacement valves, implantable sensors including glucose sensors, cardiac sensors, identity or tracking sensors (e.g., RFID), sensors to detect or measure $O_2$, pH, temperature, ions, and the like, orthopaedic implants, including tissue implants, such as facial implants for the chin, cheek, jawbone, and nose, implantable subcutaneous or percutaneous access ports, drain tubes such as Eustachian drain tubes, catheters such as urinary catheters, respiratory-assist tubes, and the like.

The collagen membrane, scaffold or covering of fibres can be configured to substantially encase the target implantable device or may cover only a portion thereof.

The collagen membrane, scaffold or covering can be a three dimensional array of fibres or fibrils held together or on the device in any suitable manner including by their natural affinity to stick together upon compression or extrusion, by using a sticky coating or adhesive, such as a gelatinous coating, or by otherwise attaching the fibres to form the array.

The term "simultaneous mechanical stimulation" used in the methods described herein refers to the process of stretching the collagen membrane during the chemical processing of the collagen-containing tissue. The membrane may undergo static and/or cyclic stretching. Accordingly, in some embodiments the simultaneous mechanical stimulation may comprise:

(i) stretching of the membrane for a preset period;
(ii) relaxation of the membrane for a preset period; and
(iii) n-fold repetition of steps (i) and (ii), where n is an integer greater than or equal to 1.

If the mechanical stimulation is carried out by stretching the membrane, the membrane is preferably stretched along its long axis.

In some embodiments, the simultaneous mechanical stimulation comprises applying tension cyclically to collagen-containing tissue, wherein the periodicity of the tension comprises a stretching period of about 10 seconds to about 20 seconds and a relaxing period of about 10 seconds, and the strain resulting therefrom is approximately 10%, and the mechanical stimulation continues until the collagen bundles within the collagen-containing tissue are aligned as described herein.

The subject invention also concerns the use of collagen membranes or scaffolds of the invention for the in vitro or in vivo delivery of bioactive compounds, drugs, growth factors, proteins, peptides, nucleic acids, inorganic or organic molecules, etc. A collagen-containing tissue or scaffold of the invention can be loaded with a bioactive compound, etc. and then the loaded scaffold can be implanted or contacted with the body, tissue, cells, etc. of a person or animal. The compounds are then permitted to be released from the scaffold into the body, tissue, cell, etc. The collagen membrane or scaffold can be provided on a biodegradable or non-degradable support structure or matrix.

The collagen used in the present invention can be synthetic or derived from any suitable animal species. The collagen can be from a vertebrate animal or an invertebrate (e.g., starfish, sea urchin, sponges, etc.). In some embodiments, the collagen is fish, shark, skate, or ray collagen. In another embodiment, the collagen is human, equine, bovine, ovine, porcine, canine, or feline collagen. In an exemplified embodiment, the collagen is bovine collagen.

Collagen-containing tissue or scaffolds of the present invention are stable both in vitro and in vivo for at least 4 weeks at body temperature.

The terms "repairing" or "repair" or grammatical equivalents thereof are used herein to cover the repair of a tissue defect in a mammalian animal, preferably a human. "Repair" refers to the formation of new tissue sufficient to at least partially fill a void or structural discontinuity at a tissue defect site. Repair does not however, mean or otherwise necessitate, a process of complete healing or a treatment, which is 100% effective at restoring a tissue defect to its pre-defect physiological/structural/mechanical state.

The term "tissue defect" or "tissue defect site", refers to a disruption of epithelium, connective or muscle tissue. A tissue defect results in a tissue performing at a suboptimal level or being in a suboptimal condition. For example, a tissue defect may be a partial thickness or full thickness tear in a tendon or the result of local cell death due to an infarct in heart muscle. A tissue defect can assume the configuration of a "void", which is understood to mean a three-dimensional defect such as, for example, a gap, cavity, hole or other substantial disruption in the structural integrity of the epithelium, connective or muscle tissue. In certain embodiments, the tissue defect is such that it is incapable of endogenous or spontaneous repair. A tissue defect can be the result of accident, disease, and/or surgical manipulation. For example, cartilage defects may be the result of trauma to a joint such as a displacement of torn meniscus tissue into the joint. Tissue defects may be also be the result of degenerative diseases such as osteoarthritis.

Typically, the collagen membrane of the invention will be implanted at the site of the tissue defect and secured in place by any conventional means known to those skilled in the art, e.g. suturing, suture anchors, bone fixation devices and bone or biodegradable polymer screws.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Method for the Manufacture of Collagen Membrane

A collagen segment from porcine inner organ lining was carefully separate and placed into a solution comprising about 70% ethanol and allowed to briefly incubate at room temperature. The collagen-containing tissue was then stretched fatty side up over the working surface and as much fat tissue and blood vessels as possible was removed.

In order to visualize fat tissue present the collagen-containing tissue was coated with glycerol for about 10 minutes. At which point the collagen was transparent, but the fat tissue was a white colour. Using forceps we separated the white fat tissue from the collagen under an anatomical microscope.

When complete, the collagen-containing tissue was carefully transferred to a sealed container and incubated in a solution comprising about 1% (v/v) SDS and 0.2% (v/v) LiCl in order to denature the non-collagenous proteins. The incubation was left overnight at 4° C.

The collagen-containing tissue was then carefully washed two times in 100% acetone to remove the denatured the non-collagenous proteins. The tissue was then centrifuged at 100 RPM in a 200 ml container in order to gently spin down residual solutions, non-collagenous proteins and nucleic acids from the collagen-containing tissue.

The collagen-containing tissue was carefully removed and once again washed in membranes Steripure™ water 3 times.

Sometimes, we also washed the collagen-containing tissue in a solution comprising NaOH:NaCl after which we centrifuged the tissue at 100 RPM for 90 minutes.

The collagen-containing tissue was then immersed in 0.5% (v/v) HCl and placed on shaker for 30 minutes to denature the collagen. We found that the concentration of HCl and incubation time was important in order to avoid damaging the mechanical structure of the resulting tissue.

The collagen-containing tissue was then removed and once again washed in Steripure™ water 3 times.

The collagen-containing tissue was then neutralized using 0.5% (v/v) NaOH. At this stage preliminary testing of the mechanical properties of resulting collagen-containing tissue could be undertaken.

The collagen-containing tissue was then manipulated using mechanical forces (compression and extension) using a stainless steel frame. Once the collagen-containing tissue was stretched to the right size, thickness and the like, the tissue was denatured in situ i.e. within the frame, immersion in a solution comprising 1% (v/v) HCl. Typically, the tissue was incubated with shaking at 100 RPM for 22-25 hours until the collagen fibre bundles had aligned.

The collagen-containing tissue was then washed with water and rinsed with mixture of 1% (v/v) SDS and 0.2% (v/v) LiCl.

Depending upon the end use, the collagen-containing tissue was then re-coated with glycerol for 10 minutes to visualise any residual fat tissue. As above, forceps were used to separate the remaining white fat tissue from the collagen under an anatomical microscope. Any extra collagen bundles are also removed at this stage in order to control the thickness of the collagen-containing tissue.

Finally, the collagen-containing tissue was treated with acetone and air-dried while still stretched within the frame so that the aligned collagen bundles became fixed. The collagen-containing tissue was then stretched, compressed and/or rolled to create a smooth surface. The finished collagen membrane tissue was then examined and cut to size using a laser cutter.

SEM was performed to characterize the surface morphology of the collagen membrane compared to other types of membranes. In brief, the tissue samples were sputter-coated with 5 nm thick platinum (SEM coating unit, E 1020, Hitachi Science Systems Ltd., Japan) and both sides were viewed under a scanning electron microscope (S260, Leica, Cambridge, England) at a low voltage (20 kV).

FIG. 1 shows the surface morphology of the collagen membrane produced by the methods of the present invention (TYMPACOL™ membrane referred to as ACS herein) compared to other membranes. Scanning electron microscopy shows the surface morphology of three scaffolds (Panel A-C; .times.500, D; .times.200). TYMPACOL™ membrane (referred to as ACS in FIG. 1) possesses two distinct surfaces, a smooth surface featuring compact collagen bundles (Panel A), and a rough, porous surface of loose collagen fibres (Panel B). Paper patch (membrane) surface is uneven with few small pores (Panel C). GELFOAM® membrane shows substantial pores of varying sizes (Panel D). Scale bar: 500 µm.

Figure 2:
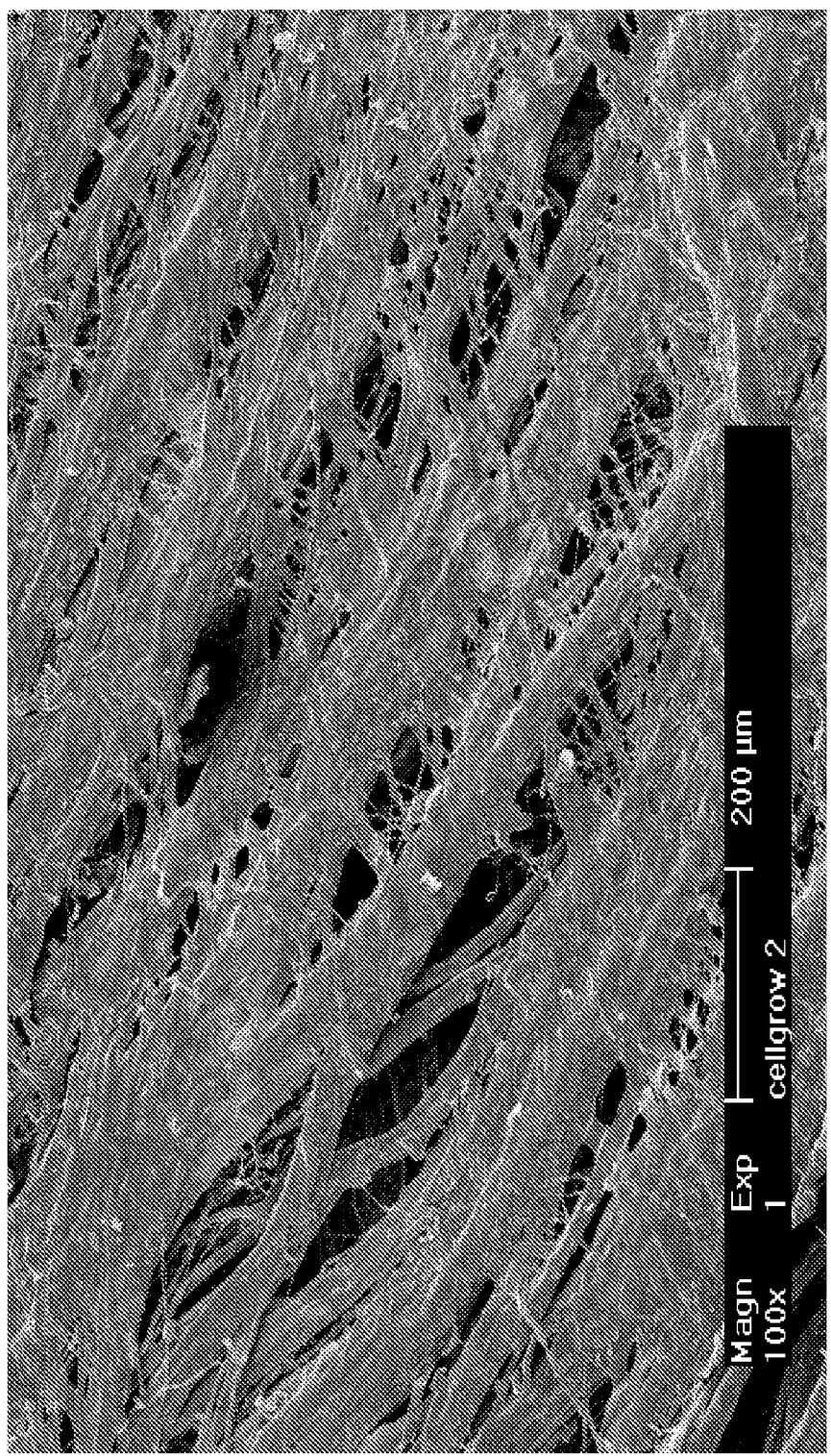
FIG. 2 shows scanning electron microscopy (SEM) image (×100) of a collagen membrane produced by the methods of the present invention.

FIG. 2 shows scanning electron microscopy (SEM) image (×100) of a collagen membrane produced by the above method.

Figure 3:
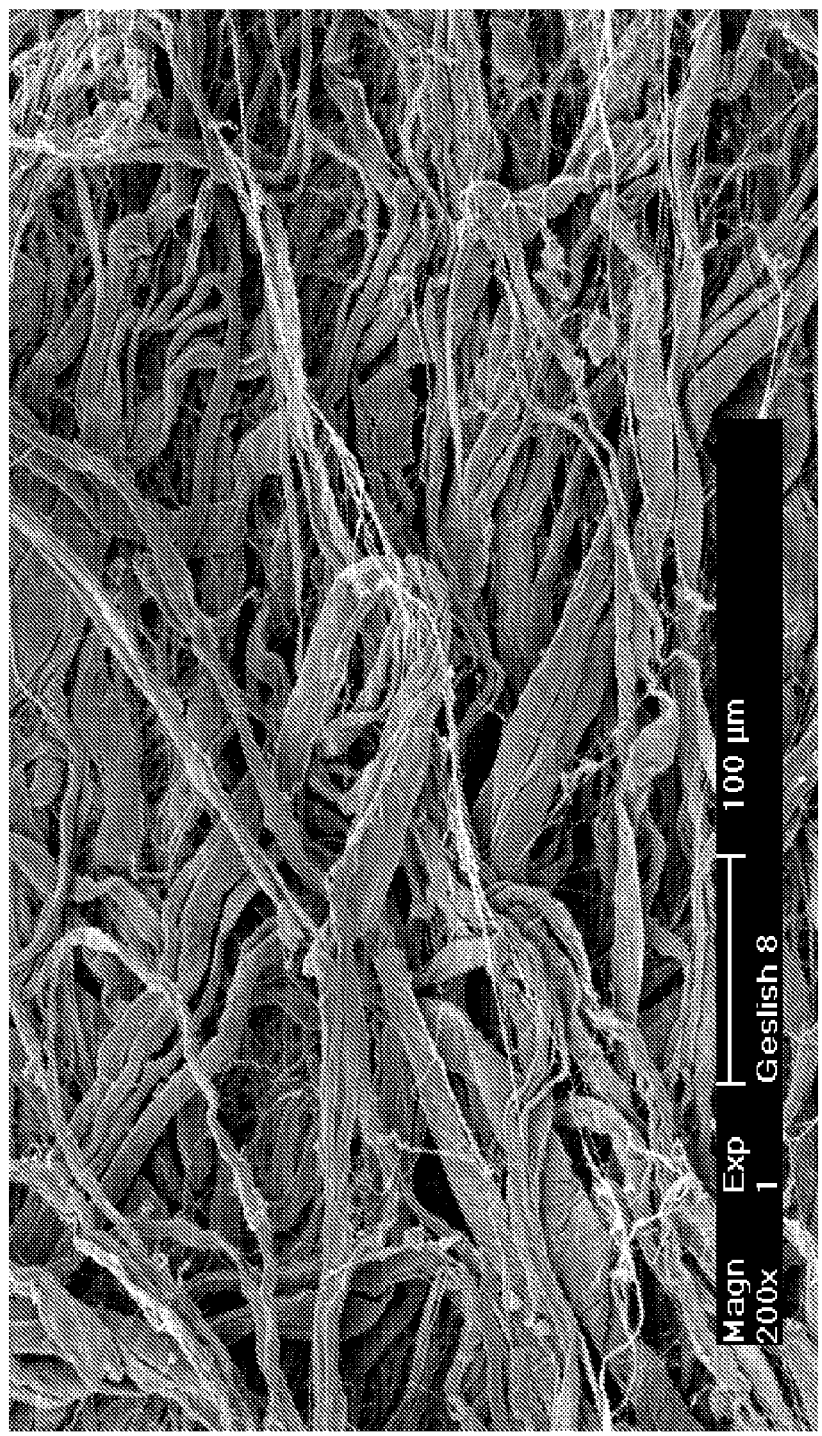
FIG. 3 shows scanning electron microscopy (SEM) image (.times.200) of a commercially available bioscaffold ("BIO-GIDE™" membrane) Luitpold Pharmaceuticals, Inc, Shirley, N.Y. USA.

FIG. 3 shows scanning electron microscopy (SEM) image (.times.200) of a commercially available bioscaffold ("BIO-GIDE™" membrane) Luitpold Pharmaceuticals, Inc, Shirley, N.Y. USA. It can be seen that the collagen bundle arrangement in the BIO-GIDE™ membrane is less uniformed than the TYMPACOL™ membrane.

Figure 4:
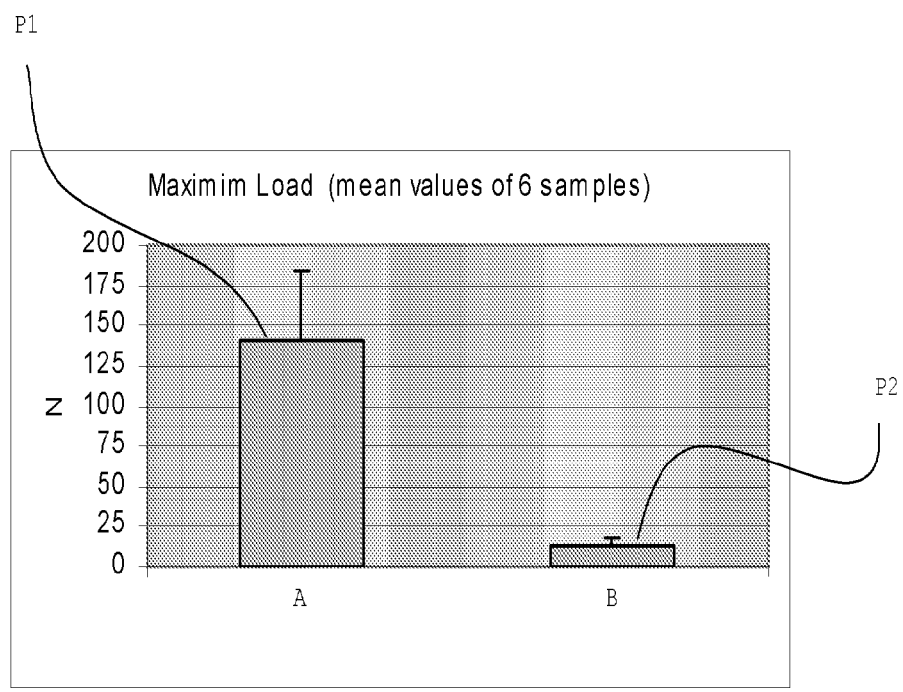
FIG. 4 shows a bar graph showing comparative mean maximum load for a collagen membrane produced by the methods of the present invention and commercially BIO-GIDE™ membrane.

FIG. 4 shows a bar graph showing comparative mean maximum load for a collagen membrane produced by the methods of the present invention and commercially BIO-GIDE™ membrane.

Figure 5:
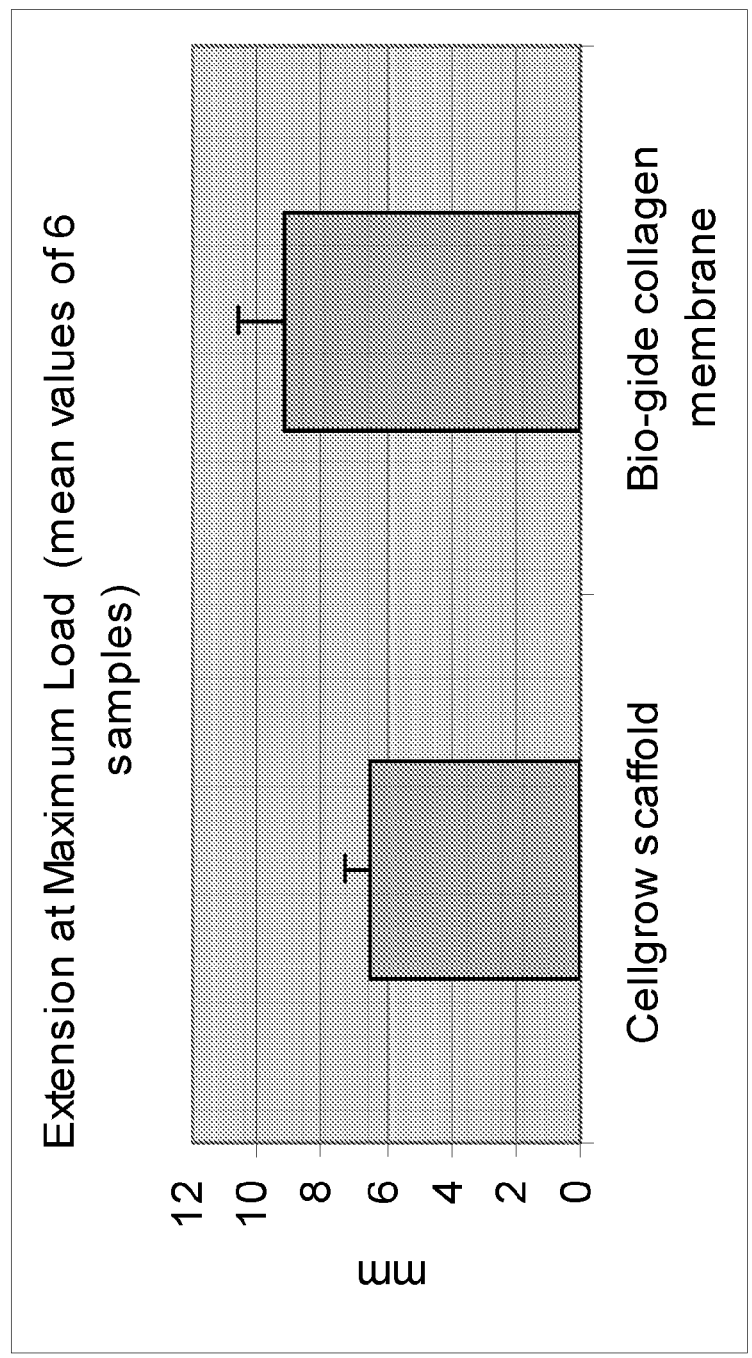
FIG. 5 shows a bar graph showing comparative mean extension at maximum load for a collagen membrane produced by the methods of the present invention and commercially BIO-GIDE™ membrane.

FIG. 5 shows a bar graph showing comparative mean extension at maximum load for a collagen membrane produced by the methods of the present invention and commercially BIO-GIDE™ membrane.

Figure 6:
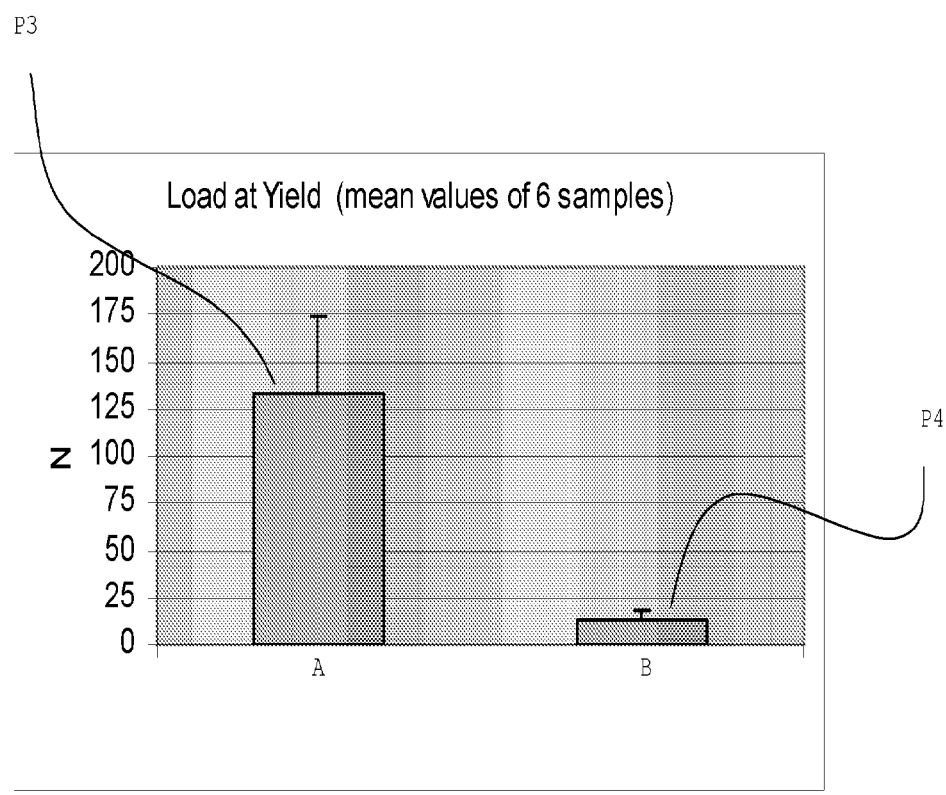
FIG. 6 shows a bar graph showing comparative mean load at yield for a collagen membrane produced by the methods of the present invention and commercially BIO-GIDE™ membrane.

FIG. 6 shows a bar graph showing comparative mean load at yield for a collagen membrane produced by the methods of the present invention and commercially BIO-GIDE™ membrane.

Figure 7:
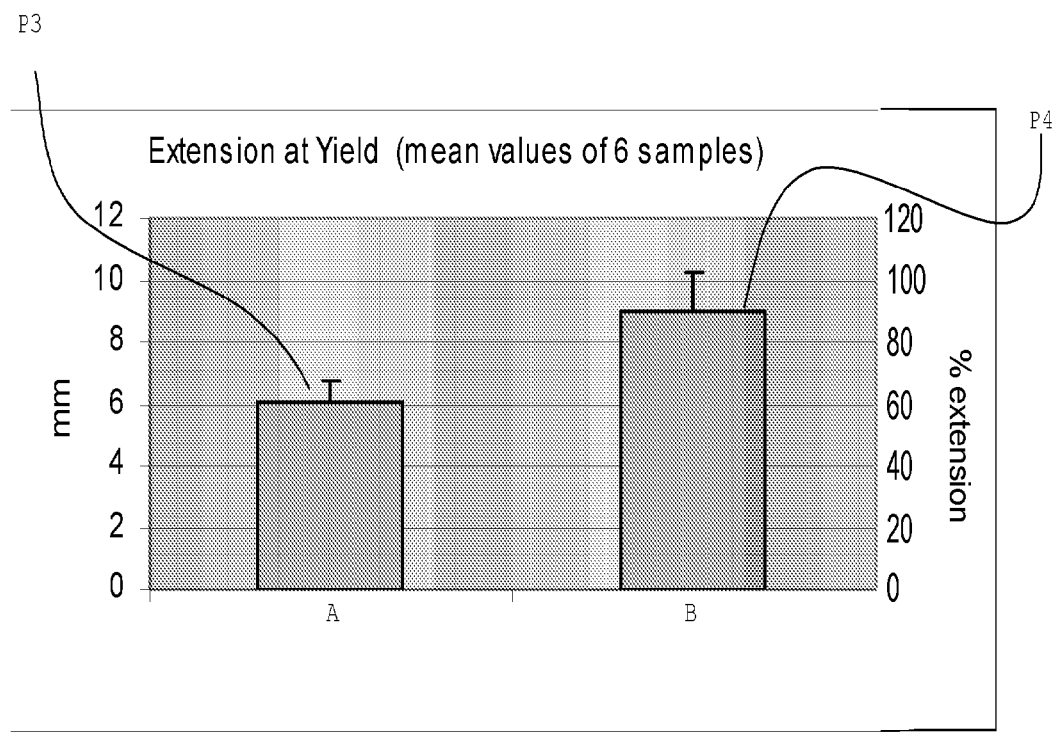
FIG. 7 shows a bar graph showing comparative mean extension at yield for a collagen membrane produced by the methods of the present invention and commercially BIO-GIDE™ membrane.

FIG. 7 shows a bar graph showing comparative mean extension at yield for a collagen membrane produced by the methods of the present invention and commercially BIO-GIDE™ membrane.

Conclusions

We found that the above method has benefits over traditional alkaline-acid methods of treating collagen-containing tissue as follows:

1) The incubation with a solution comprising 1% SDS and 0.2% LiCl enable the denaturation and removal of non-collagenous proteins and nucleic acids which are known to cause an inflammatory response with other implantable membranes.

2) Glycine coating enable the separation of fat tissue from the collagen-containing tissue which, if not removed, causes issues with the flexibility of the tissue.

3) The use of HCl together with incubation time enabled us to produce a membrane with the appropriate mechanical properties without the use of cross-linking agents such as glutaraldehyde.

4) The mechanical forces applied to the collagen membrane while it was fixed to the frame enabled us to re-arrange the collagen bundles and fibres necessary for the formation of the special structure.

5) The macro and microscopic examination on the direction of collagen bundles in the and the collagen-containing tissue shows a collagen bundle structural orientation that makes the tissue more useful in implantation studies.

Example 2

Characterisation of Collagen Membrane Compared to Other Membrane

A 40 µm thick sample of TYMPACOL™ membrane produced by the method in Example 1, was used in a clinical trial compared to commercially available membranes. The commercial products included:

1). Paper patch, which was obtained from cigarette paper (Tally Ho, Imperial Tobacco Australia, Australia) and is approximately 20 µm thick, white and opaque;

2). GELFOAM® membrane (absorbable gelatine sponge, Pharmacia & Upjohn Inc, New York, USA), is a highly absorbent, non-elastic sponge which is around 4 mm thick with pore size varying between 30-700 µm (Rohanizadeh et al., (2008), J. Materials Science; 19: 1173-1182.

Male Sprague-Dawley rats, weighing 250-300 grams, were used for the clinical trial according to the institutional animal ethic approval. Prior to the study, all animals were inspected using a S5 model otomicroscope (Zeiss, Germany) to ensure they were free of middle ear pathology. Animals were randomly divided into four scaffold repair groups, namely TYMPACOL™ membrane (n=30), paper patch (n=30), GELFOAM® membrane (n=30) and control (spontaneous healing) (n=30). In addition, a group of ten rats (n=10) were allocated as normal controls (without any perforation or scaffold).

All the surgical procedures were performed under general anaesthesia with intramuscular Ketamine (80 mg/kg) and Medetomidine (0.5 mg/kg). Debris from the external auditory canal was removed using a 3.0 mm aural speculum and the external auditory canals were prepped with povidone iodine solution. Bilateral tympanic membrane (TM) perforations, measuring approximately 1.8 mm in diameter, were created using a sterile 23-gauge needle in the posterior half of the pars tensa via a transcanal approach. Four different materials were then trimmed into pieces (2.4 mm in diameter), rinsed with 1× phosphate buffered saline solution (pH 7.4) (Invitrogen, Shanghai, China), and grafted onto the right TM perforation using on-lay myringoplasty. The left ear served as an internal control where no graft material was placed on the perforated TM. All rats were given subcutaneous buprenorphine (0.02-0.08 mg/kg) for postoperative analgesia.

The TM healing of different treatment groups was evaluated by otoscopy, scanning electron microscopy (SEM), histology and transmission electron microscopy (TEM), while the hearing function was analysed by auditory brainstem responses (ABR). In each group, the same five rats (n=5) were selected randomly for both otoscopic and ABR assessment at 3, 5, 7, 9, 14, and 28 days postoperatively. In these subgroups of five rats, three were used for histological evaluation, and one each for SEM and TEM.

Otoscopic Observation

To investigate TM healing an acute rat model of TM perforation was established. Five rats from each group were randomly chosen at each time point for otoscopic observation using a digital video otoscope (MedRX, Largo, Fla.) under general anaesthesia. The TMs were viewed by two independent observers with respect to perforation closure, infection, myringosclerosis, granulation tissue and thickening. Each TM perforation was graded as either completely closed or unclosed. Only TMs that had completely closed were considered healed. Digital images were recorded using Aurisview software (Ear Science Institute Australia, Subiaco, Australia).

SEM was performed to evaluate the healing process of TM following repair by scaffolds. Briefly, the rat TM specimens were fixed with 2.5% glutaraldehyde in 4° C. overnight, dehydrated in ethanol solutions followed by critical point drying (HCP-2, Hitachi, Tokyo, Japan). Finally, the samples were coated with 5 nm thick platinum where the medial surface of the TMs was observed under SEM.

All rats survived the surgical procedures with no complications postoperatively. The lateral aspect of TMs was observed via an otoscope to assess the effect of grafting at each time point. No signs of infection or abnormalities were observed in any of the rats.

In the control group, the TMs appeared thicker and opaque post-perforation, with prominent microvessels visible close to the perforation margin. By 14 days, the TM became increasingly transparent and majority of the perforations had fully closed. At 28 days, all the perforations were completely healed, although visible scars resembling an opalescent ring were observed at the perforation site. The semi-transparency of TYMPACOL™ membrane allowed direct observation of the TM healing. Throughout the healing process, TYMPACOL™ membrane retained its structural stability and adhered well to the TM remnant. The opacification of TM and microvessel was less pronounced compared to those in the control group. The perforations had healed as early as 7 days after grafting where the healed TMs appeared normal. In contrast, paper patch and GELFOAM® membrane were opaque, making it difficult to examine the middle ear during healing. Moreover, these materials tended to detach easily from the healing TM. In particular, the bulk of GELFOAM® membrane shrank and its porous structure was lost over time. At 28 days, the TMs in the paper patch and GELFOAM® membrane groups appeared healed but with some scarring.

Following sacrifice at individual time points, closure of the perforation was confirmed by observing the internal surface of the harvested TMs using an otomicroscope. TM healing in the TYMPACOL™ membrane groups was markedly quicker compared to the other groups (FIG. 10). 60% (3/5) of TYMPACOL™ membrane treated ears were completely healed but none in the control group had healed (0/5) ($p<0.05$). After 9 days, the TM was completely healed in all five rats in the TYMPACOL™ membrane and paper patch groups, which was significantly different compared to the control group (2/5) ($p<0.05$). At 14 days, all ears were completely healed except one TM in the control group (4/5). By 28 days post surgery, all the TMs had completely healed.

Histological Evaluation

Following sacrifice, both external ears were separated at the osteocartilaginous junctions and the TMs along with the bony annulus were removed from the tympanic bulla. Harvested specimens were fixed in 10% neutral buffered formalin for 24 hours followed by decalcification in 10% ethylenediaminetetraacetic acid solution (EDTA) (pH 7.4) for two to three weeks. Decalcified TMs were dehydrated in a series of graded alcohols, embedded in paraffin wax and transversely sectioned at a thickness of 4 µm. All sections were evaluated using haematoxylin and eosin (H&E) staining. Masson's trichrome staining was performed to examine the morphology of collagen fibres. All stained slides were digitally scanned using an Aperio ScanScope XT automated slide scanner (Aperio Technologies Inc., Vista, Calif.; 40×/0.75 Plan Apo objective). Images were saved as TIFFs for histological evaluation. TM thickness of healed TM sections of day 14 and 28 was measured using Aperio ImageScope Viewer software.

The histology of the TM healing and effects of the four scaffolds were examined over 28 days. Compared to other groups, TM healing in the control group was relatively slower. In the first week, the perforation remained patent, although hyperplasia was observed in the epithelial and connective tissue (CT) layers of the TM. On day 5, a keratin spur was seen and the perforations started to close at 9 days with significant thickening throughout the three TM layers. By 28 days, the healed TM became thinner but with residual thickening at the previous perforation site. The CT layer was found to be disorganized with loosely packed collagen fibres (FIG. 8).

In the TYMPACOL™ membrane treated group, epithelial hyperplasia and vascular proliferation were evident in the early stages. Infiltrating cells resembling fibroblasts were abundant in the CT layer with occasional lymphocytes surrounding the graft. At 28 days, the healed TM appeared normal with a trilaminar structure (FIG. 8).

In contrast, numerous inflammatory cells (predominantly lymphocytes) and prominent exudate was observed surrounding the paper patch. Although the TM perforation eventually healed, the TM remained thickened with disorganization of the newly synthesized fibres (FIG. 8). Likewise, GELFOAM® membrane induced the infiltration of inflammatory cells at implanted site. Unlike other materials, prominent fibroblast proliferation and erythrocyte-filled blood vessels were found in the CT layer. After 28 days, the healed TM remained thickened with atypical disorganized collagen fibres in the CT layer (FIG. 8).

Figure 8:
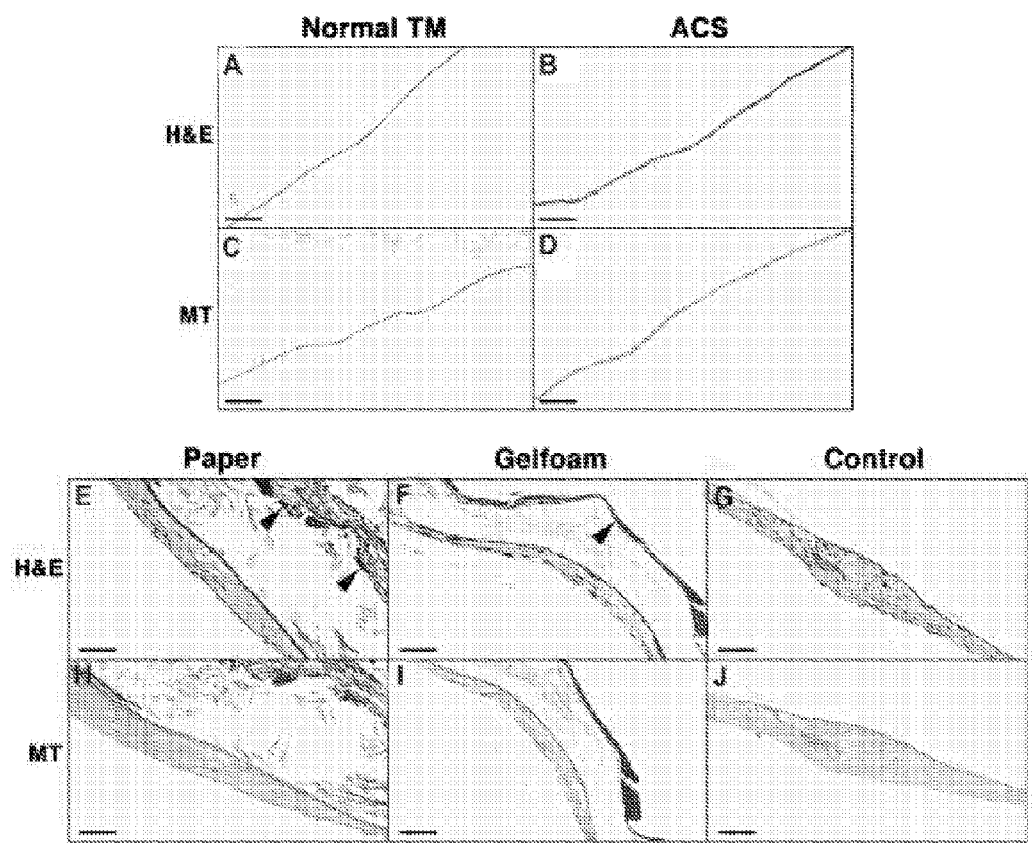
FIG. 8 shows photomicrographs of healed tympanic membranes (TMs) 28 days following grafting of a collagen membrane produced by the methods of the present invention compared to other commercially available membranes. Normal TMs stained with H&E (Panel A) and Masson trichrome (MT) (Panel C) are shown. At 28 days, TMs treated with TYMPACOL™ membrane (ACS (Panels B & D)) had normal trilaminar structure, consisting of dense and well-organized collagen bundles in the CT layer. TMs treated with paper patch (Panels E, H) and GELFOAM® membrane (Pfizer, Puurs, Belgium) (Panels F, I) remained thickened in the healed area with loose and disorganized collagen fibres in the middle layer. TMs in the control group (Panels G, J) remained thick with atypical structure and regions of irregular collagen fibres. At 14 days, all TMs were significantly thickened compared to the normal TM (Panel K). By 28 days, TMs thickness in the ACS groups showed no significant differences compared to the normal TMs (Panel L). (*$p<0.05$, **$p<0.01$). Arrowheads indicate the residual scaffolds. H&E and Masson trichrome staining Scale bars: 50 µm.
Figure 8:
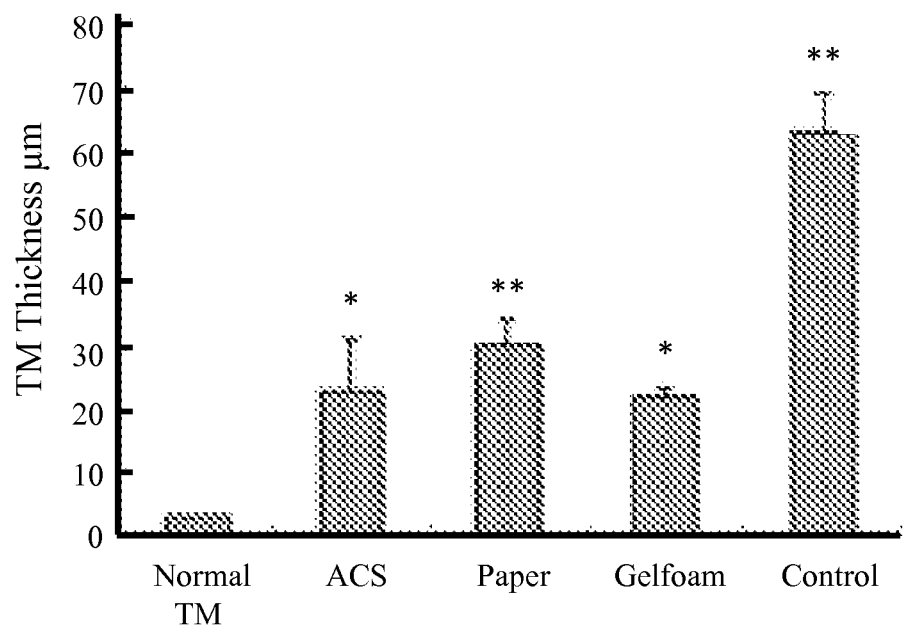
Figure 8:
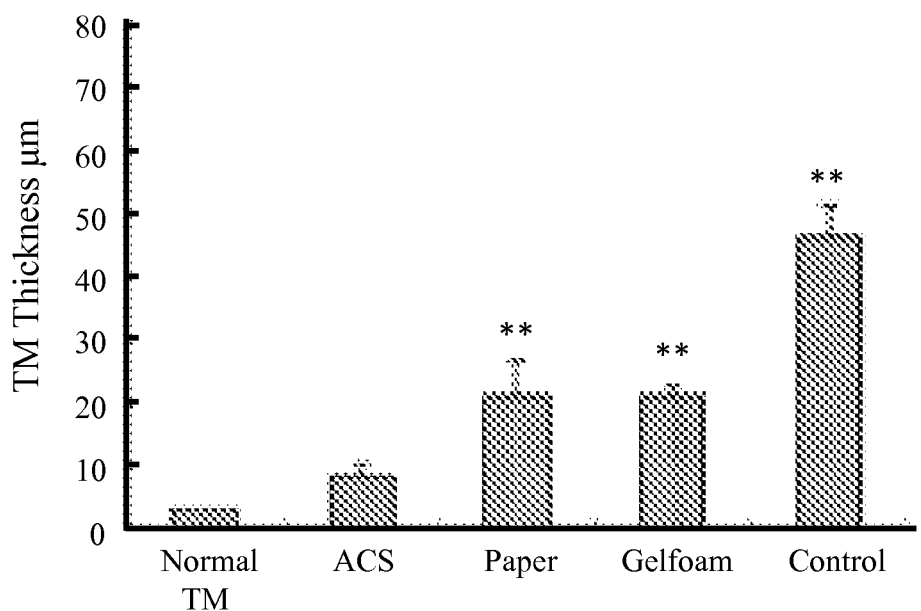

The TM cross-sections were used to quantify changes in the TM thickness following treatment (FIG. 8). At 14 days, TMs in all groups were substantially thickened compared to normal TM ($p<0.05$) except SFS treated TM, which had similar thickness (14.13±4.04 µm) to the normal TM ($p>0.05$). By 28 days, statistically significant difference in TM thicknesses was found in the control, paper patch and GELFOAM® membrane groups ($p<0.05$). However, no statistically significant difference in TM thicknesses was seen between TYMPACOL™ membrane groups (8.55±4.25 µm) compared with the normal TM ($p>0.05$).

Transmission Electron Microscopy (TEM)

TEM was performed to investigate the microstructure of the healed TMs on day 28 post-repair. Briefly, following dissection, the perforation site of the harvested TM samples was fixed in 2.5% glutaraldehyde and stored overnight at 4° C. Tissue specimens were washed, postfixed (1% osmic acid), dehydrated and embedded for transmission observation. Thin transverse sections were cut and examined with TEM (TECNAI 10, Philips Co., Netherlands) at 80 kV.

TEM observation was performed to investigate the ultrastructure of healed TMs 28 days post-surgery. In TYMPACOL™ membrane treated and spontaneously healed TMs, the CT layer was moderately thickened and fibroblast accumulation was apparent compared to the normal TM. In TYMPACOL™ membrane group, the three layers of the TM were readily identified, and the CT layer was compact with collagen bundles well-orientated. However, in paper patch and GELFOAM® membrane groups, collagen fibres were loosely and irregularly arranged in the fibrous layer, with obvious edema seen.

The medial aspect of TMs was observed with SEM to assess scaffold attachment, cellular integration with scaffold and perforation closure. TYMPACOL™ membrane showed steady attachment to the perforation margin throughout the healing process, thereby preserving their scaffold function. TM epithelial cells migrated across the wound margin and adhered to the internal surface of to TYMPACOL™ membrane on day 5. By 9 days, the TMs of TYMPACOL™ membrane group had healed and the internal surface of neo-membranes was smooth. In contrast, paper patch demonstrated early partial detachment from the TM surface, but its scaffold function partially lost. Exudate formation and inflammatory cell infiltration was evident at the perforation site in the paper group. GELFOAM® membrane showed early disintegration of its sponge structure. As shrinkage and absorption progressed, most of the GELFOAM® membrane dissolved, resulting in loss of its support function. The healed TMs in paper and GELFOAM® membrane groups showed some scarring at 14 days. In the control group with no scaffold implantation, a rolled perforation edge of the unhealed TM was visible at 9 days. The TM eventually healed by 14 days, but with an obvious scar.

Auditory Brainstem Responses (ABR)

To assess the hearing of rats following grafting, ABR was performed using the Nihon Kohden Neuropack-μ Measuring Systems (MEB-9100, Nihon Koden, Japan) in a soundproof room. Rats were anesthetized before testing as previously described. Platinum subdermal needle electrodes were inserted at the scalp vertex (active electrode), both mastoids (reference electrode) and at the nose tip (ground electrode). The test stimuli (click) with 0.1 ms duration were presented through an insert earphone. Animals were presented with a stimulus intensity series from 90- to 0 dB sound pressure level (SPL) in 10 dB decrements. A total of 512 responses were averaged in each series of stimuli over a 10 ms analysis period. Thresholds were defined as the lowest intensity to elicit a reproducible ABR waveform with typical wave III or wave IV morphology. Auditory thresholds of click stimuli were measured pre- and post TM perforation in the right ear of all rats, and at each time point after myringoplasty for the five animals from each group. The normal ears and the ears with TM perforation without materials served as controls.

Figure 9:
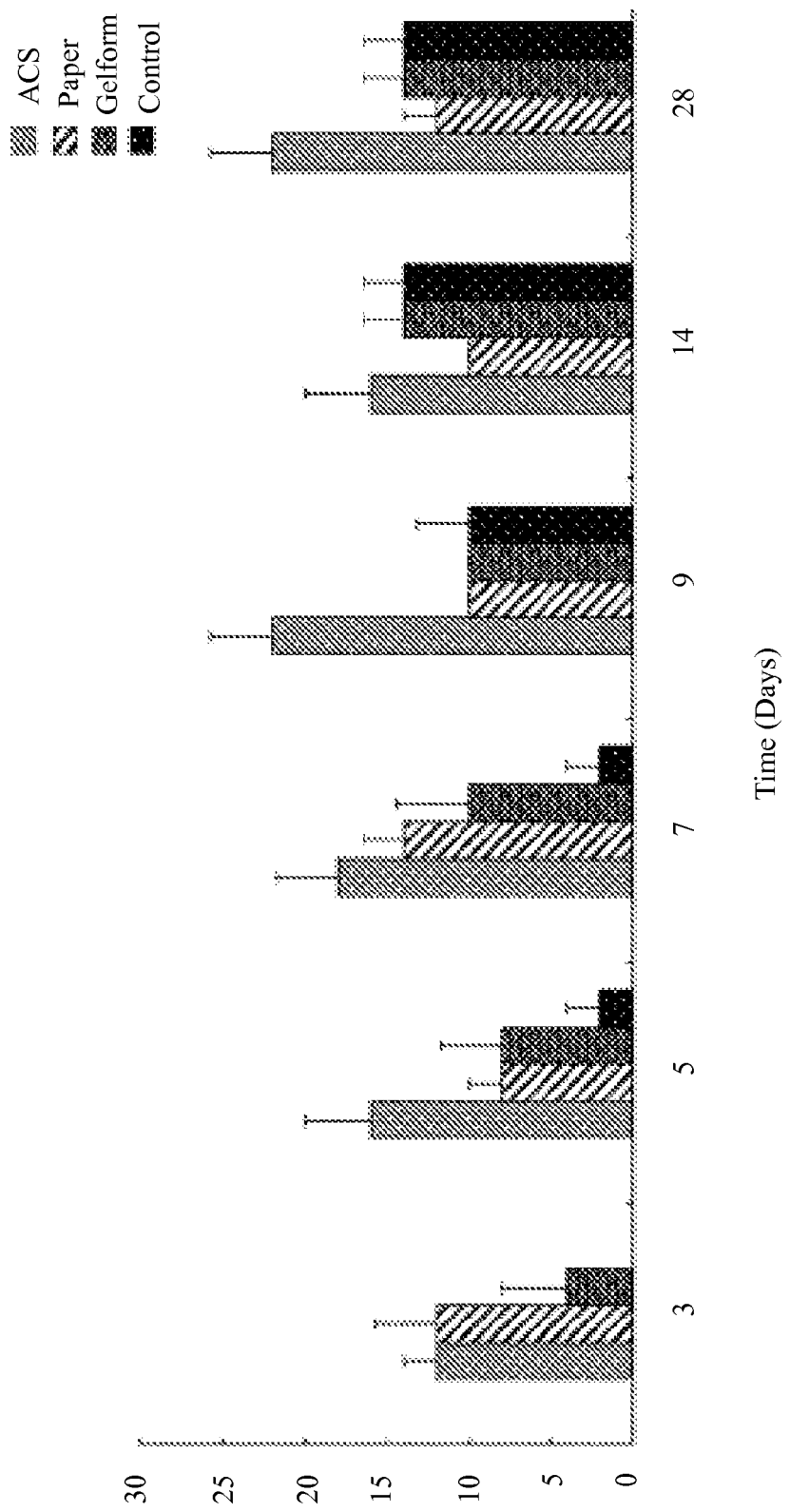
FIG. 9 shows auditory brainstem responses assessment of hearing recovery following grafting. The hearing recovery was defined as the difference between auditory threshold immediately following perforation (pre-repair) and at specific time points following grafting (post-repair). The values represent mean±standard error of mean (SEM) (n=5). Hearing recovery following grafting in each group was performed using multiple linear regression analysis. Auditory threshold of all rats recovered over time and significant differences were observed when comparing between different treatments ($p<0.01$). Hearing in the rats treated by the ACS recovered significantly faster compared to those treated with paper patch, GELFOAM® membrane and spontaneous healing (control). Statistical significance between groups was: a ACS and spontaneous healing (p<0.01); ACS and paper (p<0.01); ACS and GELFOAM® membrane (p<0.01).

Hearing thresholds were similar in all treatment groups that measured pre-perforation ($p>0.05$) as well as post-perforation ($p>0.05$). The average auditory threshold of normal rat was 15.0 dB and this was significantly increased to 29.5 dB after perforation, indicating that TM perforation caused significant hearing loss ($p<0.01$). Audiometric assessment using ABR demonstrated hearing recovery for all groups following treatment (FIG. 9). The hearing recovery was defined as the difference between auditory threshold immediately following perforation (pre-repair) and at specific time points following grafting (post-repair). Auditory threshold of all rats recovered over time, and significant differences were observed when comparing between different treatments ($p<0.01$). Most obviously, hearing in the animals treated with TYMPACOL™ membrane recovered significantly faster compared to those treated with paper patch ($p<0.01$), GELFOAM® membrane ($p<0.01$) and spontaneous healing ($p<0.01$).

Statistical Analysis

Healing rates determined by otoscopic observation were compared using the chi-square ($\chi^2$) test. Statistical analysis for ABR and TM thickness was evaluated using one-way analysis of variance (ANOVA) whereas hearing recovery in each group over time was performed using multiple linear regression analysis. All analyses were performed using the Statistical Software R (Version 2.11.1, package meta). Statistical significance was defined as $p<0.05$.

Conclusion

This study demonstrated that the collagen membrane of the present invention (TYMPACOL™ membrane) significantly shortened the perforation closure time and promoted TM wound healing compared to two commonly used scaffolds (paper patch and GELFOAM® membrane) and spontaneous healing in a rat model. The healed TMs in TYMPACOL™ membrane groups showed improved morphology with regeneration of compact collagen fibres, rapid return to a normal TM thickness, as well as complete hearing recovery at an earlier stage compared to the other groups. As the goals of surgical treatment for TM perforation are to achieve complete closure of the perforation and restoration of the hearing, these results suggest that TYMPACOL™ membrane is efficient and will serve as an ideal scaffold to restore both TM healing and hearing.

Biocompatibility of a scaffold is an important element to consider, as inflammatory response following the application of biomaterials may lead to failure in surgery. Collagen is also known to elicit minimal inflammatory and antigenic responses. Pachence. (1996), J. biomed. Mat. Res.; 33:35-40). In this study, the TYMPACOL™ membrane accelerated and improved TM healing, partly attributed to minimal inflammatory response at the implantation sites.

In this study, we showed that TYMPACOL™ membrane achieved significantly faster hearing recovery compared to the other groups. We postulate that these improvement result from improved organization of collagen fibres of healed TMs and early remodelling to achieve comparable thickness to a normal TM.

TYMPACOL™ membrane was found to be easy to handle during surgery as it was not as fragile as paper or bulky and spongy as GELFOAM® membrane. Moreover, the transparency of TYMPACOL™ membrane allowed direct observation of the TM, whereas the opacity of paper and GELFOAM® membrane obstructed the direct visibility of TM healing. From a clinical point of view, these characteristics make TYMPACOL™ membrane more favorable compared to paper and GELFOAM® membrane.

The invention claimed is:

1. A method of producing a collagen-containing membrane comprising the steps of:
   (i) isolating a collagen-containing tissue and incubating the isolated collagen-containing tissue in an ethanol solution;
   (ii) incubating the isolated collagen-containing tissue from step (i) in a solution comprising about 1% (v/v) SDS and about 0.2% (v/v) LiCl in order to denature non-collagenous proteins contained therein;

(iii) incubating the collagen-containing tissue produced in step (ii) in a solution comprising about 0.5% (v/v) HCl until the collagen in said material is denatured; and (iv) incubating the collagen-containing tissue produced in step (iii) in a solution comprising about 1% (v/v) HCl with simultaneous mechanical stimulation for sufficient time to enable the collagen bundles in said collagen-containing tissue to align; wherein the mechanical stimulation comprises applying tension cyclically to the collagen-containing tissue, thereby producing said collagen-containing membrane.

2. The method of claim 1, wherein the ethanol solution comprises greater than 70% ethanol.

3. The method of claim 1, wherein the incubation in step (ii) is at about 4° C.

4. The method of claim 1, wherein the incubation in step (ii) is undertaken for at least 12 hours.

5. The method of claim 1, wherein the incubation in step (iii) is undertaken for about 30 minutes.

6. The method of claim 1, wherein the incubation in step (iii) is undertaken with shaking.

7. The method of claim 1, wherein the incubation in step (iv) is undertaken for about 12 to 36 hours.

8. The method of claim 7, wherein the incubation in step (iv) is undertaken for about 24 hours.

9. The method of claim 1, wherein the incubation in step (iv) is undertaken with shaking.

10. The method of claim 1, further comprising a neutralization step between step (iii) and step (iv) which comprises incubation of said collagen-containing tissue with about 0.5% (v/v) NaOH.

11. The method of claim 1, further comprising step (v) which comprises incubating the collagen-containing tissue from step (iv) with acetone and then drying the collagen-containing tissue.

12. The method of claim 1, wherein between steps (ii) and (iii) and/or between steps (iii) and (iv) the collagen-containing tissue is contacted with glycerol in order to visualise and facilitate the removal of fat and/or blood vessels.

13. The method of claim 12, wherein the glycerol is contacted with the collagen-containing tissue for at least 10 minutes.

14. The method of claim 1, wherein between steps (ii) and (iii) and/or between steps (iii) and (iv) the collagen-containing tissue is washed.

15. The method of claim 14, wherein the wash used between steps (ii) and (iii) is acetone to remove the denatured proteins.

16. The method of claim 15, wherein the collagen-containing tissue is further washed after the acetone with sterile water.

17. The method of claim 15, wherein the collagen-containing tissue is further washed in a NaOH:NaCl solution.

18. The method of claim 1, wherein after steps (iv) the collagen-containing tissue is washed with sterile water.

19. The method of claim 18, wherein the collagen-containing tissue is further washed after the sterile water with the first solution.

20. The method of claim 1, wherein the collagen-containing tissue comprises dense connective tissue.

21. The method of claim 1, wherein the collagen-containing tissue is isolated from a sheep, a cow, a pig or a human.

22. The method of claim 1, wherein the collagen-containing tissue is isolated from a human.

23. The method of claim 1, wherein the collagen-containing tissue is autologous.

* * * * *